(12) United States Patent
Becht

(10) Patent No.: US 7,261,463 B2
(45) Date of Patent: Aug. 28, 2007

(54) METHOD AND APPARATUS FOR SUPPORTING A DENTAL X-RAY SENSOR

(76) Inventor: Darrell A. Becht, 3200 Pleasant Valley La., Arlington, TX (US) 76015

( * ) Notice: Subject to any disclaimer, the term of this patent is extended or adjusted under 35 U.S.C. 154(b) by 0 days.

(21) Appl. No.: 11/182,261

(22) Filed: Jul. 15, 2005

(65) Prior Publication Data

US 2006/0013365 A1 Jan. 19, 2006

Related U.S. Application Data

(60) Provisional application No. 60/588,454, filed on Jul. 16, 2004.

(51) Int. Cl.
*A61B 6/14* (2006.01)
(52) U.S. Cl. .................. 378/168; 378/170
(58) Field of Classification Search ........ 378/167–170, 378/174, 175–176
See application file for complete search history.

(56) References Cited

U.S. PATENT DOCUMENTS

| 4,707,847 | A | 11/1987 | Van Aken | 378/170 |
|---|---|---|---|---|
| 4,815,117 | A | 3/1989 | Waldo | 378/168 |
| 4,949,370 | A | 8/1990 | Tanaka | 378/170 |
| 5,677,537 | A | 10/1997 | Pfeiffer | 250/370.09 |
| 6,033,111 | A * | 3/2000 | Winters et al. | 378/170 |
| 6,461,038 | B2 | 10/2002 | Pellegrini et al. | 378/191 |
| 6,527,442 | B2 | 3/2003 | Carroll | 378/189 |
| 2003/0152196 | A1* | 8/2003 | Bratslavsky et al. | 378/170 |
| 2005/0259791 | A1* | 11/2005 | Strong | 378/168 |

OTHER PUBLICATIONS

Website pages of net32.com, www.net32.com, 10 pp., illustrating prior art sensor holding devices, copyright 1997-2006.
Website pages of Dentsply International, www.dentsply.com, 2 pp., describes holders for digital dental sensors, copyright 2004.
Website pages of Dentrix Dental Systems, Inc., www.dentrix.com, 4 pp., describes CCD image sensors for dental use, copyright 2005.

* cited by examiner

*Primary Examiner*—Hoon Song
(74) *Attorney, Agent, or Firm*—Whitaker, Chalk, Swindle & Sawyer, LLP; Stephen S. Mosher

(57) ABSTRACT

There is disclosed a method and apparatus for positioning an electronic dental X-ray sensor in a dental patient's mouth comprising the steps of: selecting a film positioner having an easel supported on a formed rod; assembling the electronic sensor to the film positioner to form a sensor assembly; covering the sensor with a syringe sleeve; and positioning the sensor assembly so that the electronic sensor is in position in the patient's mouth for recording an X-ray image.

2 Claims, 3 Drawing Sheets

METHOD AND APPARATUS FOR SUPPORTING A DENTAL X-RAY SENSOR

CROSS REFERENCE TO RELATED APPLICATION

The present U.S. Patent Application claims priority from earlier filed U.S. Provisional Patent Application Ser. No. 60/588,454, filed Jul. 16, 2004 and entitled "Method and Apparatus for Supporting a Dental X-Ray Sensor."

BACKGROUND OF THE INVENTION

1. Field of the Invention

The present invention generally relates to dental X-ray equipment and, more particularly, to apparatus and methods for positioning and supporting dental X-ray sensors within the mouth of a dental patient.

2. Description of the Prior Art

Traditionally, film for obtaining X-ray images of a person's teeth have been packaged in a cardboard or plastic carrier that includes a tab to be folded outward at approximately a right angle. The carrier is positioned alongside of the teeth and the patient is instructed to bite down against the tab of the carrier that is placed between the teeth to be imaged on the sensitized film within the carrier when exposed to the X-ray energy. A disadvantage of this system is that the carrier is a stiff, thin material that is uncomfortable for many patients because it tends to dig into the patient's cheek.

In a conventional alternative to the film carrier with the fold-out tab, the film carrier is placed on a wand-like positioner tool that places the carrier in position in the patient's mouth without having to bite down on it. While more comfortable, it requires that someone hold the positioner in the correct position to expose the film correctly.

Recent advances in the electronic arts have produced an X-ray sensor device that substitutes for the film carrier. It is positioned and exposed similarly to the traditional film carrier but has the significant advantage that it records the image electronically, obviating the conventional film development process. However, the problem remains as to how best to hold the sensor in position in the patient's mouth. The sensor lacks a tab to bite down upon and must be held in position by other means. What is needed is a device and/or method of positioning the sensor that is comfortable, easy to use, and provides consistent, repeatable results in the X-ray images.

SUMMARY OF THE INVENTION

Accordingly there is disclosed a method for positioning an electronic dental X-ray sensor in a dental patient's mouth comprising the steps of: selecting a film positioner having an easel supported on a formed rod; assembling the electronic sensor to the film positioner to form a sensor assembly; covering the sensor with a syringe sleeve; and positioning the sensor assembly so that the electronic sensor is in position in the patient's mouth for recording an X-ray image. The sensor is assembled to the positioner using an adhesive pad to the outer side of the easel of the positioner; attaching the electronic sensor to a second side of the adhesive pad; and routing the signal lead of the adhesive pad away from the sensor and the formed rod of the positioner.

In another aspect, there is disclosed an apparatus for positioning an electronic dental X-ray sensor in a dental patient's mouth comprising: a film positioner having an easel having an outer side and supported at a distal end of a formed rod attached to the easel; an electronic dental X-ray sensor having a mounting surface and at least one signal lead; and an adhesive pad having first and second opposing sides, each side coated with a non-toxic, low-tack adhesive, wherein the adhesive pad is pressed between the outer side of the easel and the mounting surface of the sensor to form an assembly. The assembly is enclosed in a syringe sleeve.

DETAILED DESCRIPTION OF THE INVENTION

Figure 1:
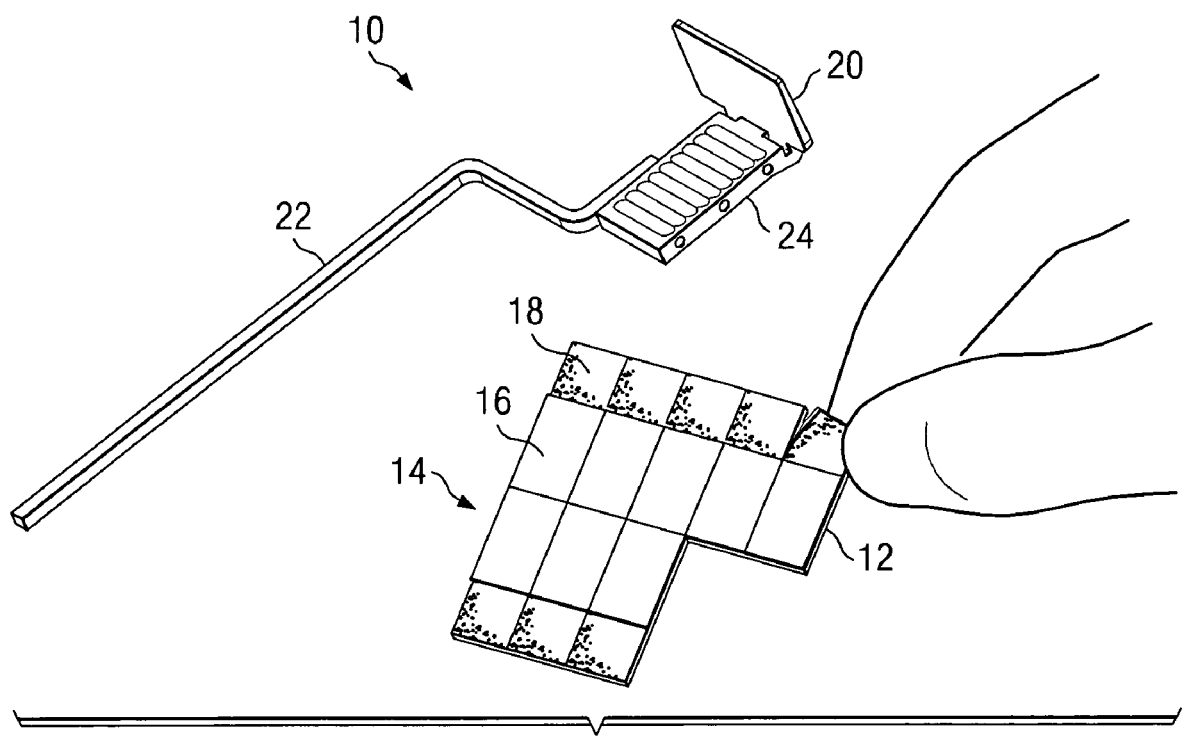
FIG. 1 illustrates step one of a method and apparatus for positioning an electronic dental x-ray sensor according to the disclosed invention.

Referring to FIG. 1, there is illustrated the first of a set of steps one through six of a method and apparatus for positioning an electronic dental x-ray sensor according to the disclosed invention. The method makes use of an adhesive pad, also called a SensorStik (trademark registration applied for) device, a small rectangle of non-toxic, synthetic foam having a low tack adhesive applied to at least a portion of each planar side of the rectangle. The rectangle is approximately 12 mm×56 mm×2.5 mm in dimensions. The adhesive on each planar side is protected by a peel-off strip that is removed just before use. The SensorStik devices or adhesive pads may, for example, be conveniently furnished in packages of two dozen foam devices along with illustrated instructions for use.

Before proceeding with step one, the user is instructed as follows. Remember to glove up (put on a pair of sterile gloves) before placing an x-ray sensor in a patient's mouth to avoid cross-contamination. For those who use a type of sleeve that holds the sensor snugly to a positioner, rather than an air-water syringe sleeve, the adhesive on the SensorStik adhesive pad is non-toxic, but you may want to use a new one for each shot. The SensorStik adhesive pad is a versatile device and works with many of the sensor devices presently on the market.

In step one, FIG. 1, after putting on the sterile gloves and choosing the correct positioner assembly 10 for a particular x-ray image, grasp the SensorStik adhesive pad 12 by the non-adhesive portion, separate the selected adhesive pad 12 from the panel 14 of adhesive pads 12, and peel off the adhesive backing 16 from a first side of the adhesive pad 12, as shown.

Figure 2:
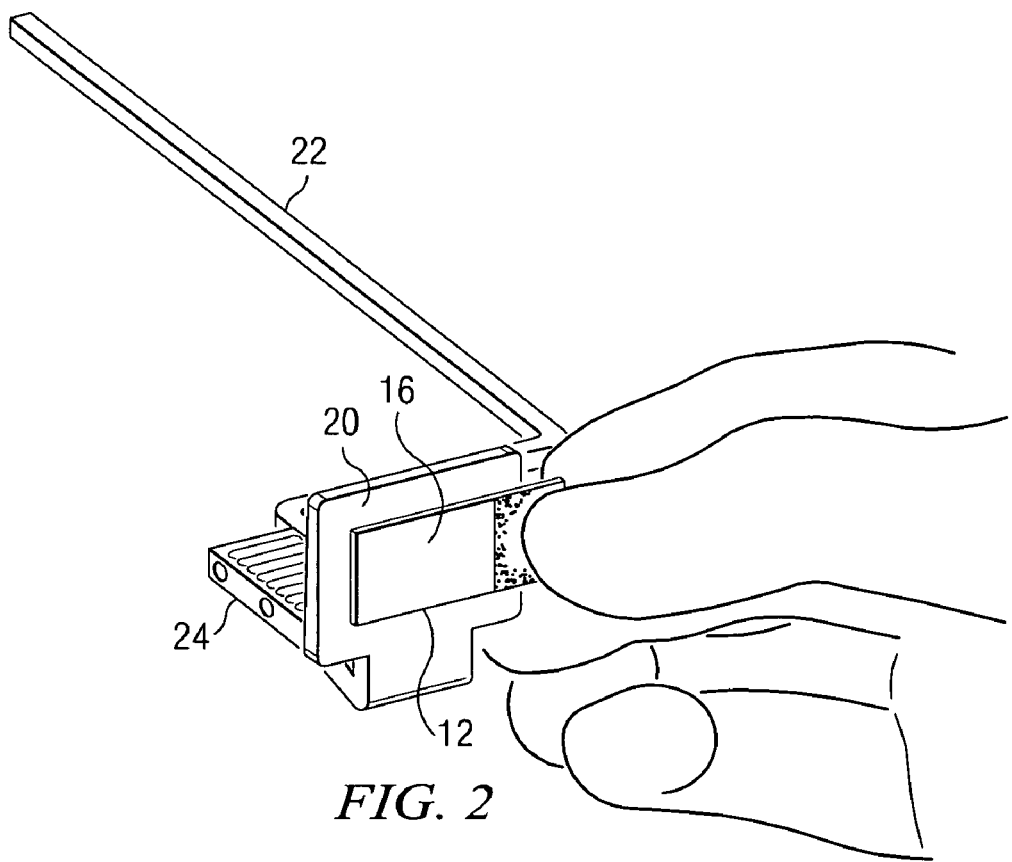
FIG. 2 illustrates step two of the method and apparatus for positioning an electronic dental x-ray sensor according to the disclosed invention.

In step two, FIG. 2, attach the side of the SensorStik adhesive pad 12 having the exposed adhesive to your normal film holder 20, also called an easel 20 herein. Note that the correct side of the film holder or easel 20 is the outer side, opposite the positioner rod 22, as shown in FIG. 2 for step two.

Figure 3:
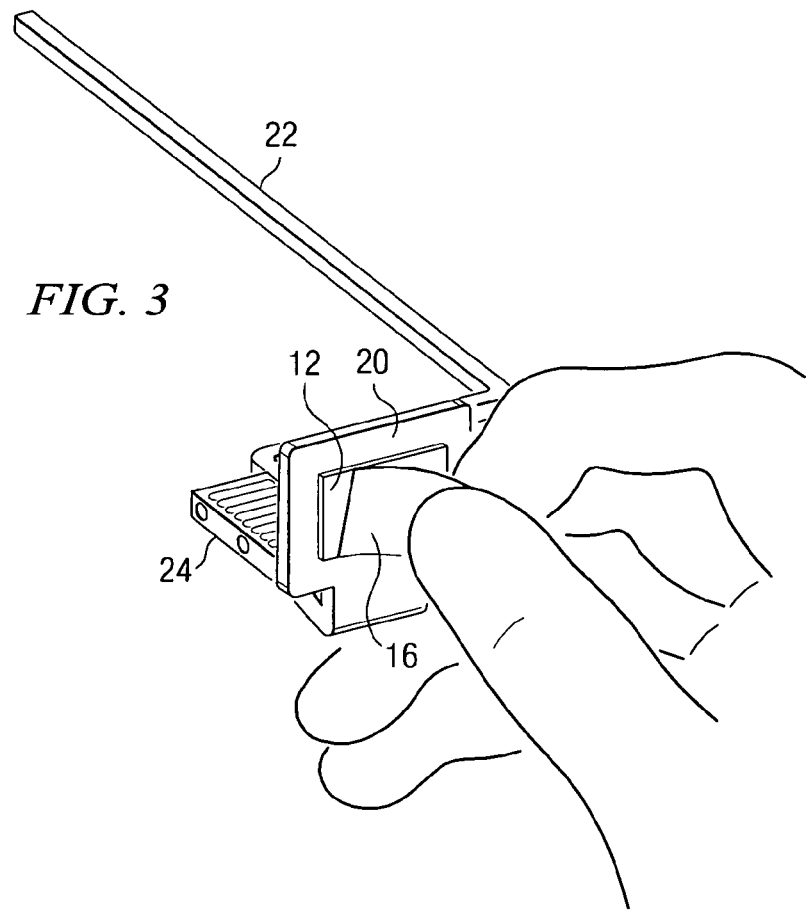
FIG. 3 illustrates step three of the method and apparatus for positioning an electronic dental x-ray sensor according to the disclosed invention.

In step three, FIG. 3, carefully peel off the adhesive backing on the second or remaining side (not shown) of the SensorStik adhesive pad 12, making sure that the glove does not touch the adhesive surface. The reason for this is that most gloves will leave behind enough powder to interfere with the adhesion of the SensorStik adhesive pad 12 to the sensor 26 when it is attached in the next step.

Figure 4:
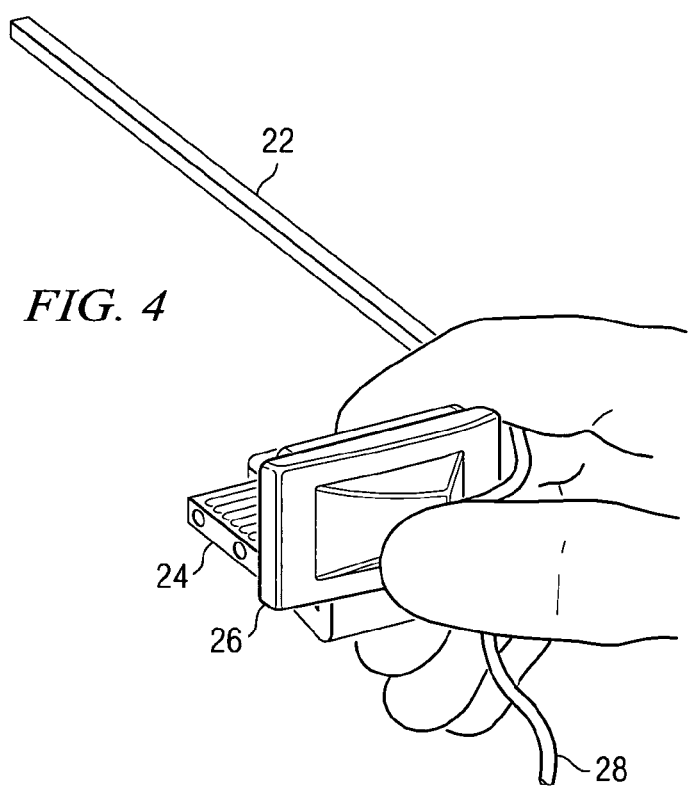
FIG. 4 illustrates step four of the method and apparatus for positioning an electronic dental x-ray sensor according to the disclosed invention.

In step four, FIG. 4, place the flat side of the sensor 26 against the exposed adhesive of the adhesive pad 12, and squeeze gently to make sure the sensor 26 is held firmly in place. Try to install the sensor 26 above the extension portion of the film holder 20 to avoid getting images of the positioner rod 22 or other artifacts in the x-ray image. Also, if the weight of the particular sensor 26 requires two SensorStik adhesive pads 26 to support it, then do so.

Figure 5:
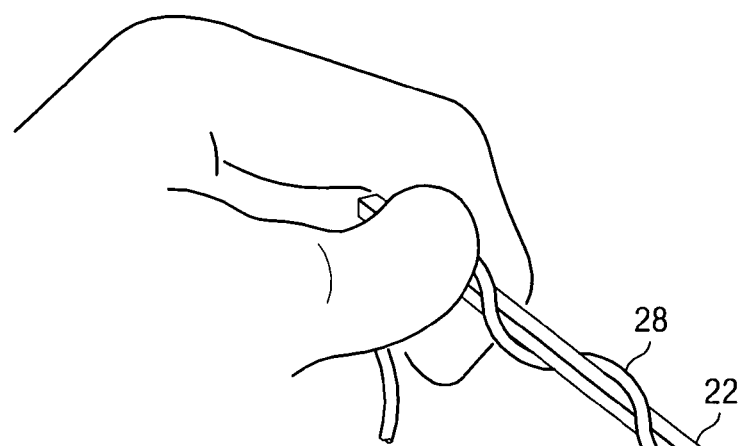
FIG. 5 illustrates step five of the method and apparatus for positioning an electronic dental x-ray sensor according to the disclosed invention.

In step five, FIG. 5, drape the sensor wire 28 gently around the positioner rod 22 to hold it out of the way. Do not wrap it tightly, to avoid straining the sensor wire 28. Also, be careful not to drape the sensor wire 28 between the x-ray head and the surface of the sensor 26, to avoid an artifact that may result.

Figure 6:
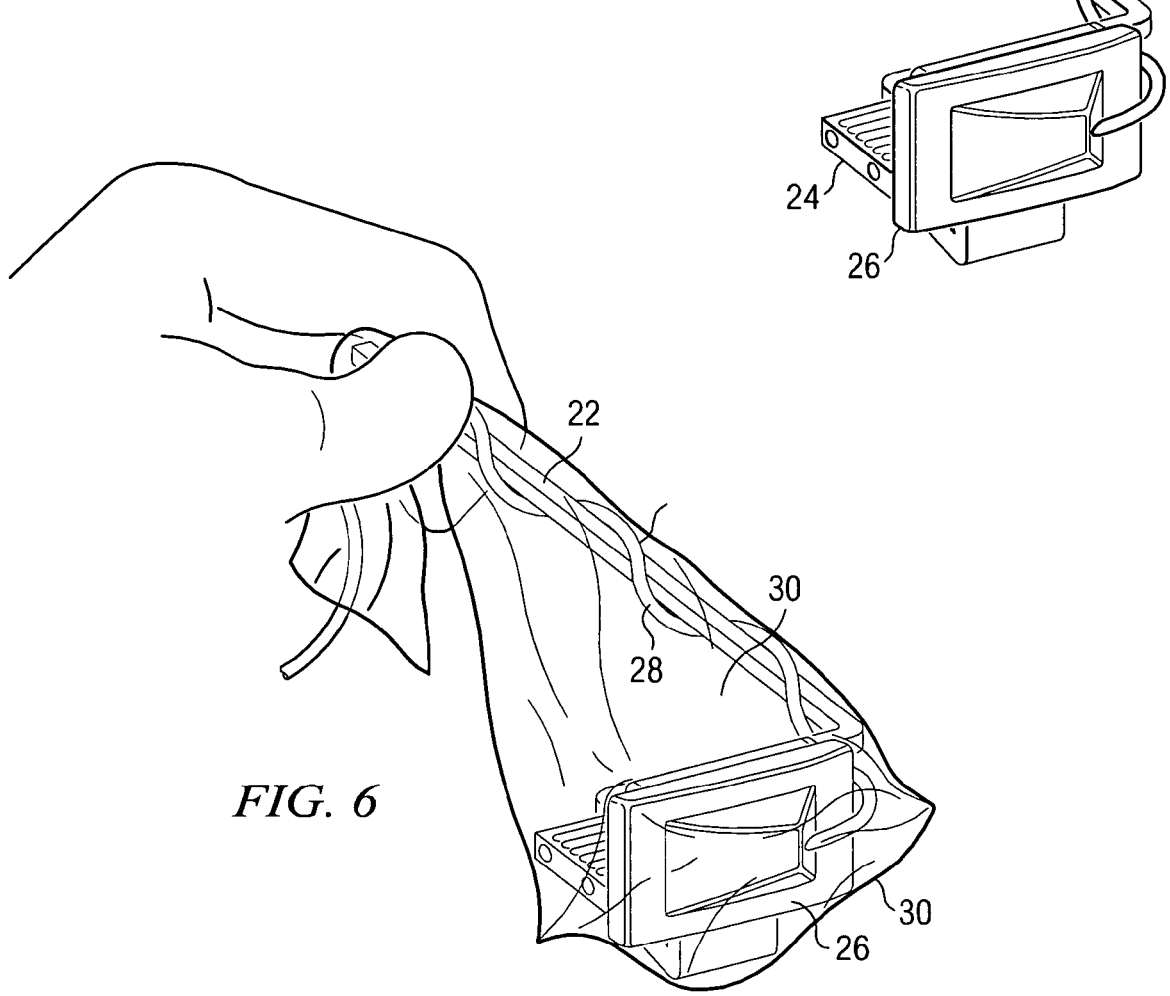
FIG. 6 illustrates step six of the method and apparatus for positioning an electronic dental x-ray sensor according to the disclosed invention.

In step six, FIG. 6, using an air-water syringe sleeve 30 (be sure to avoid using one with holes or openings) cover the sensor 26 and positioner assembly 10. Once the syringe sleeve 30 is in place, as well as between x-ray exposures, the sensor 26 and film holder 20 may need to be squeezed to re-secure the sensor 26 to the film holder 20, then expose the x-ray sensor 26 to form the image.

While the invention has been shown in only one of its forms, it is not thus limited but is susceptible to various changes and modifications without departing from the spirit thereof.

What is claimed is:

1. A method for positioning an electronic dental x-ray sensor having a signal lead in a dental patient's mouth, comprising the steps of:
   selecting a film positioner assembly having an easel supported on a formed rod;
   assembling the electronic sensor to the film positioner assembly to form a sensor assembly;
   covering the sensor assembly with a syringe sleeve; and
   positioning the sensor assembly so that the electronic sensor is in position in the patient's mouth for recording an x-ray image;
   wherein the step of assembling comprises the steps of:
   attaching a first side of an adhesive pad to the outer side of the easel of the film positioner assembly;
   attaching the electronic sensor to a second side of the adhesive pad; and
   routing the signal lead away from the electronic sensor and along the formed rod of the film positioner assembly.

2. An apparatus for positioning an electronic dental x-ray sensor in a dental patient's mouth, comprising:
   a film positioner having an easel having an outer side and supported at a distal end of a formed rod;
   the electronic dental x-ray sensor having a mounting surface and at least one signal lead; and
   an adhesive pad having first and second opposing sides, each side coated with a non-toxic, low tack adhesive, wherein the adhesive pad is pressed between the outer side of the easel and the mounting surface of the sensor to form an assembly; and
   a syringe sleeve for enclosing the assembly.

* * * * *